(12) United States Patent
Kawabe

(10) Patent No.: US 7,742,565 B2
(45) Date of Patent: Jun. 22, 2010

(54) METHOD AND APPARATUS FOR ANALYSIS USING X-RAY SPECTRA

(75) Inventor: Kazuyasu Kawabe, Tokyo (JP)

(73) Assignee: JEOL Ltd., Tokyo (JP)

( * ) Notice: Subject to any disclaimer, the term of this patent is extended or adjusted under 35 U.S.C. 154(b) by 85 days.

(21) Appl. No.: 12/249,209

(22) Filed: Oct. 10, 2008

(65) Prior Publication Data
US 2009/0310748 A1    Dec. 17, 2009

(30) Foreign Application Priority Data
Oct. 16, 2007    (JP)    ............. 2007-268963

(51) Int. Cl.
*G01T 1/36* (2006.01)
(52) U.S. Cl. ........................................ 378/82
(58) Field of Classification Search ............ 378/41, 378/42, 70, 82
See application file for complete search history.

(56) References Cited

U.S. PATENT DOCUMENTS 4,885,465 A * 12/1989 Nagatsuka et al. ............ 850/10
5,912,940 A * 6/1999 O'Hara ........................ 378/82
2006/0193434 A1 * 8/2006 Green ......................... 378/57

FOREIGN PATENT DOCUMENTS

| JP | 51-25184 A | 3/1976 |
|---|---|---|
| JP | 01-312449 A | 12/1989 |
| JP | 2002-181745 A | 6/2002 |

* cited by examiner

*Primary Examiner*—Irakli Kiknadze
(74) *Attorney, Agent, or Firm*—The Webb Law Firm

(57) ABSTRACT

A method for precisely measuring and displaying the whole profile of an X-ray spectral waveform, which rises from a background level and finally returns to the background level after passing across a peak. X-rays are counted for a time interval of to at a spectral position, resulting in X-ray N counts not containing statistical fluctuations. A standard deviation Eo representing a variation accompanying the N counts is given by Sqrt(N). Where the variation is greater than a given magnitude (tolerance error Er for display) at a spectral position where the X-ray intensity is high, X-rays are counted for a time interval of tm longer than the time interval to, producing increased counts Nm.

14 Claims, 6 Drawing Sheets

METHOD AND APPARATUS FOR ANALYSIS USING X-RAY SPECTRA

BACKGROUND OF THE INVENTION

1. Field of the Invention

The present invention relates to a method and apparatus for X-ray analysis using a wavelength-dispersive X-ray spectrometer (WDS) and, more particularly, to measurement and display of X-ray spectra.

2. Description of Related Art

Electron probe microanalyzers (EPMAs) and X-ray fluorescent analyzers (XRF) measure X-ray spectra and perform qualitative and quantitative analyses, using wavelength-dispersive X-ray spectrometers (WDS).

FIG. 4 is a diagram illustrating the principle of WDS equipped to an EPMA. This X-ray spectrometer has a curved X-ray analyzing crystal whose center C moves on a straight line that is tilted by a takeoff angle a from a point S from which X-rays are produced. At this time, the point S, center C, and the center D of a slit in the X-ray detector are kept on a Rowland circle having a constant radius of R. Furthermore, the distance SC is kept equal to the distance CD. The analyzing crystal C having a crystal lattice plane curved with a radius of curvature of 2R always faces the center O of the Rowland circle.

The distance SC is referred to as the spectral position L. Let $\theta$ be the angle of incidence of X-rays on the analyzing crystal. As can be seen from FIG. 4, the following relationship holds:

$$L = 2R \times \sin\theta \quad (1)$$

Meanwhile, regarding the diffraction conditions for the analyzing crystal, the following relationship holds:

$$2d \times \sin\theta = n \times \lambda \quad (2)$$

where $\lambda$ is the wavelength of X-rays and d is the lattice interplanar spacing of the analyzing crystal. n is a diffraction order assuming a positive integer. Eqs. (1) and (2) lead to $$L = (2R/2d) \times n \times \lambda \quad (3)$$

The relationship between the wavelength $\lambda$ of X-rays and the spectral position L can be known from Eq. (3).

An X-ray spectrum having a horizontal axis on which wavelength $\lambda$ (or any one of a corresponding energy value, spectral position L, the value of $\sin\theta$, and the value of $2\theta$) is plotted and a vertical axis on which X-ray intensity is plotted can be obtained by scanning across the spectral position L and, at the same time, measuring X-rays that are counted by an X-ray detector.

Characteristic X-rays produced from chemical elements constituting a substance have wavelengths intrinsic to the respective elements. The kinds of the elements contained in a sample to be analyzed can be known by knowing the wavelength $\lambda$ of the characteristic X-rays (qualitative analysis). The concentrations of the contained elements can be known by knowing the intensities of the characteristic X-rays (qualitative analysis). For example, JP-A-2002-181745 sets forth a conventional technique for performing a simple quantitative analysis by collecting X-ray spectra by WDS, identifying chemical elements from the spectra, and making a comparison with the previously found X-ray intensity of a reference sample using the characteristic X-ray peaks of the identified elements.

Counting of X-rays involves a random process. When the average of collected counts is N, the variance based on statistical fluctuations also produces N counts. Therefore, in the conventional X-ray spectrum acquired under the condition where the count time per point is kept at a constant value, collected counts near peak tops have the greatest amount of variation (statistical fluctuations). Consequently, it is impossible to obtain accurate waveforms from short-time measurements where the count time per point is constant.

FIG. 5 is a graph showing the results of a simulation made to know whether the profile of a spectrum near peak tops having some height is affected by the presence or absence of variations in X-ray X counts. A spectrum (P) is obtained on the assumption that peaks having no variations are derived. In contrast, a spectrum (Q) is obtained based on X-ray counts in a case where X-ray counts collected at various spectral positions are subjected to variations due to a random process.

In order to obtain an accurate X-ray spectral waveform by minimizing variations in X-ray counts, one conventional technique consisting of increasing the constant count time per point corresponding to each spectral position is available. The whole X-ray spectrum has been measured for a long time. In another conventional method available, the whole X-ray spectrum is measured in a short time. Then, a region close to peaks is again measured for a long time.

However, these techniques fail to meet a demand for a technique capable of performing an analysis in a practically minimum time. Therefore, JP-A-51-25184 discloses a technique for lowering the scanning speed of a spectrometer only near existing peaks after detecting whether there are characteristic X-ray peaks. Furthermore, JP-A-1-312449 discloses a technique consisting of preparing a sample to be analyzed, previously setting a wavelength range for the sample, and making a long measurement of only the wavelength range in which characteristic X-ray peaks of chemical elements that might be contained in the sample appear.

In the technique of JP-A-51-25184, as the scanning speed of the spectrometer is lowered near peaks, the feed speed of a chart on which an X-ray spectrum is recorded is lowered synchronously. However, measurements of X-ray spectra using recent EPMA or XRF are performed by highly sophisticated digital control systems and so no chart is used. Furthermore, if X-ray intensities exceed a preset background level, the measure taken is only to switch the scan speed of the spectrometer to a lower speed. If peak heights vary variously, the lower speed used after the switching is kept constant irrespective of peak heights. Because characteristic X-ray peaks have heights that are different by plural orders of magnitude, it is impossible to set the scan speed according to the various peak heights.

In the technique of JP-A-1-312449, an X-ray spectrum is accepted as digital data under computer control. A wavelength range near characteristic X-ray peaks that are forecasted to appear is simply measured under constant conditions. It is impossible to set measurement conditions according to different peak heights.

SUMMARY OF THE INVENTION

It is an object of the present invention to provide a method and apparatus for precisely measuring the whole profile of an X-ray spectral waveform starting at a background level, passing across a peak, and returning to the background level in one operation in bare minimum time and for displaying the waveform.

A first embodiment of the present invention that achieves the foregoing object provides a method of X-ray analysis using an X-ray spectrum obtained by a wavelength-dispersive X-ray spectrometer that detects and spectrally disperses X-rays produced from a sample irradiated with a beam of charged particles or X-rays. The method of X-ray analysis starts with making variable a time for which X-rays are counted at each spectral position. The obtained X-ray counts are converted into X-ray counts to be collected per given count time. The magnitude of variation caused by statistical fluctuations of the X-ray counts to be collected per given count time is made equal to or less than a previously specified tolerance value at any spectral position. The X-ray spectrum is obtained using the X-ray counts obtained by the conversion.

A second embodiment of the present invention is based on the first embodiment and further characterized in that the X-ray spectrum is displayed based on the counts per given count time obtained by the conversion.

A third embodiment of the present invention is based on the first embodiment and further characterized in that the sample is analyzed quantitatively by using the counts per given count time obtained by the conversion as counts collected from characteristic X-ray peaks arising from elements contained in the sample.

A fourth embodiment of the present invention is based on the first or second embodiment and further characterized in that a reference count time for which X-rays are counted at the spectral positions is previously set and that the count rates at the spectral positions are found from counts collected for the reference count time and from the reference count time.

A fifth embodiment of the present invention is based on the fourth embodiment and further characterized in that a time for which counting is continued at the spectral positions after passage of the reference count time is determined based on (i) the count rates at the spectral positions, (ii) the reference count time, and (iii) the tolerance value.

A sixth embodiment of the present invention is based on the fourth or fifth embodiment and further characterized in that the reference count time is used as the given count time.

A seventh embodiment of the present invention is based on the first or second embodiment and further characterized in that the X-ray wavelength axis of the X-ray spectrum or an axis corresponding to the X-ray wavelength axis indicates at least one of wavelength, energy, a spectral position indicative of the distance from a point at which X-rays are produced to the center of an analyzing crystal, the value of $2\theta$, the value of $\theta$, and the value of $\sin \theta$, where $\theta$ is the scattering angle of the analyzing crystal.

An eighth embodiment of the present invention provides an X-ray analysis apparatus using an X-ray spectrum obtained by a wavelength-dispersive X-ray spectrometer that detects and spectrally disperses X-rays produced from a sample irradiated with a beam of charged particles or X-rays. A time for which X-rays are counted at each spectral position is made variable. The obtained X-ray counts are converted into X-ray counts to be collected per given count time. The magnitude of variation caused by statistical fluctuations of the X-ray counts to be collected per given count time is made equal to or less than a previously specified tolerance value at any spectral position. The X-ray spectrum is obtained using the X-ray counts obtained by the conversion.

A ninth embodiment of the present invention is based on the eighth embodiment and further characterized in that the X-ray spectrum is displayed based on the counts per given count time obtained by the conversion.

A tenth embodiment of the present invention is based on the eighth embodiment and further characterized in that the sample is analyzed quantitatively by using the counts per given count time obtained by the conversion as counts collected from characteristic X-ray peaks arising from elements contained in the sample.

An eleventh embodiment of the present invention is based on the eighth or ninth embodiment and further characterized in that a reference count time for which X-rays are counted at the spectral positions is previously set and that the count rates at the spectral positions are found from the counts collected for the reference count time and from the reference count time.

A twelfth embodiment of the present invention is based on the eleventh embodiment and further characterized in that a time for which counting is continued at the spectral positions after passage of the reference count time is determined based on (i) the count rates at the spectral positions, (ii) the reference count time, and (iii) the tolerance value.

A thirteenth embodiment of the present invention is based on the eleventh or twelfth embodiment and further characterized in that the reference count time is used as the given count time.

A fourteenth embodiment of the present invention is based on the eighth or ninth embodiment and further characterized in that the X-ray wavelength axis of the X-ray spectrum or an axis corresponding to the X-ray wavelength axis indicates at least one of wavelength, energy, a spectral position indicative of the distance from a point at which X-rays are produced to the center of the analyzing crystal, the value of $2\theta$, the value of $\theta$, and the value of $\sin \theta$, where $\theta$ is the scattering angle of the analyzing crystal.

According to the present invention, an X-ray spectral waveform having the desired accuracy can be obtained in one measurement and in minimum time by determining a tolerable variation value according to the accuracy of waveform to be obtained prior to the measurement and obtaining the X-ray spectrum. Furthermore, standardless quantitative values of elements contained at high concentrations and producing characteristic X-rays of high peak intensities can be accurately found from the X-ray spectrum obtained as described above.

Other objects and features of the invention will appear in the course of the description thereof, which follows.

DESCRIPTION OF THE PREFERRED EMBODIMENTS

Figure 1:
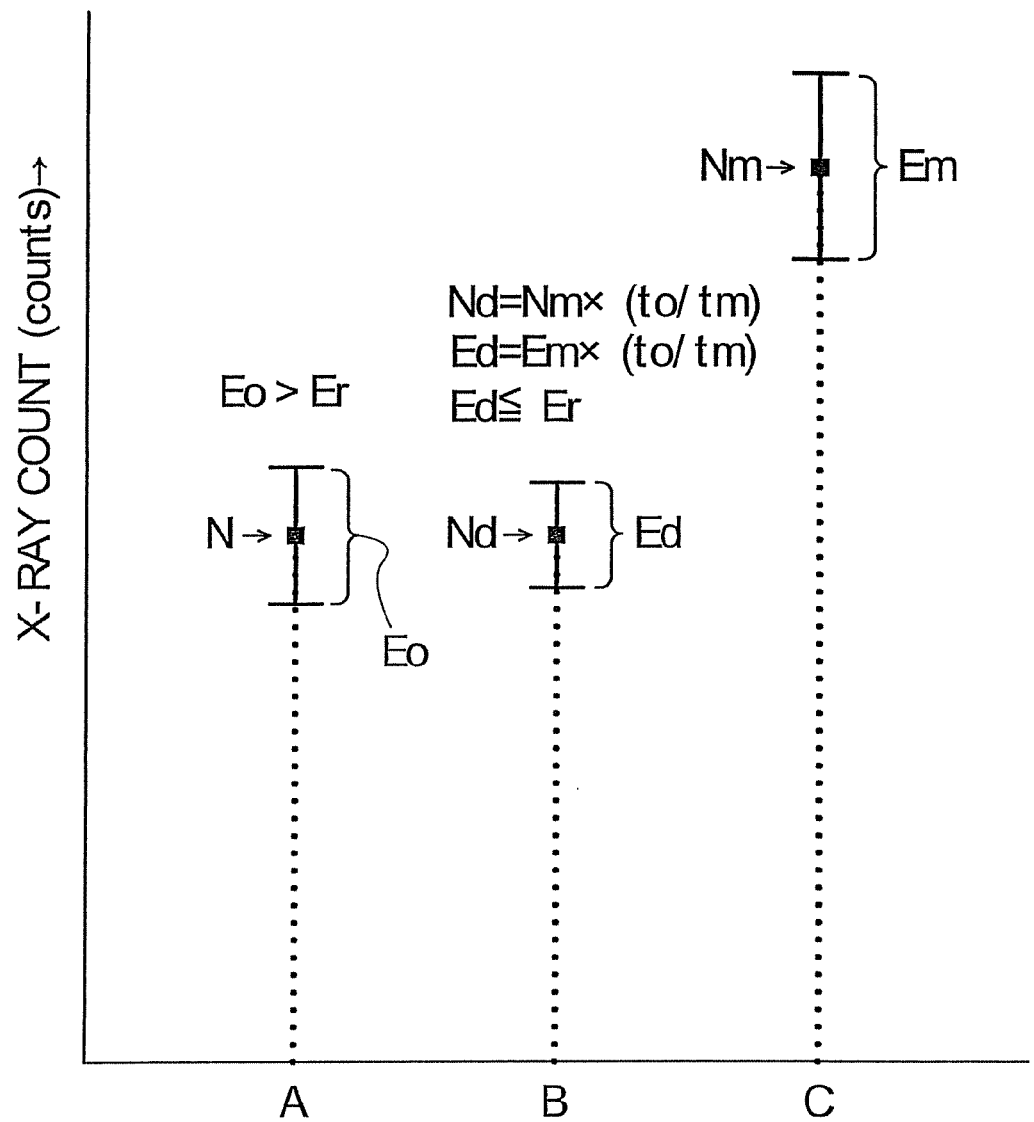
FIG. 1 is a diagram illustrating the concept of the present invention.

Embodiments of the present invention are hereinafter described with reference to the accompanying drawings. It is to be noted, however, that the technical scope of the invention is not limited thereby. In the various figures, those components operating identically or similarly are indicated by the same reference numerals and their repeated detailed description will be omitted.

Figure 2:
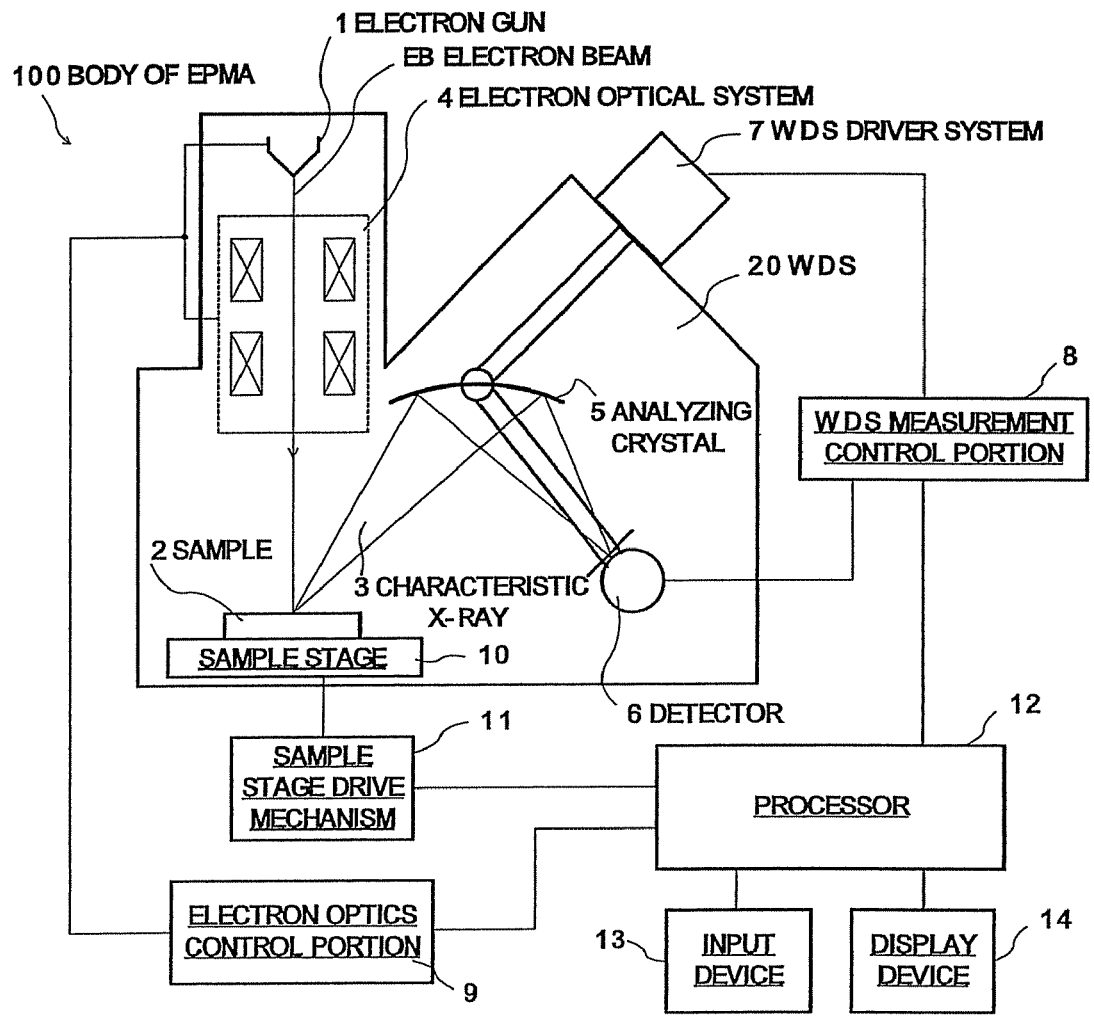
FIG. 2 is a schematic block diagram of an EPMA for embodying the present invention.

FIG. 2 is a block diagram of an EPMA (electron probe microanalyzer), schematically showing one example of configuration for implementing the present invention. The body of the EPMA is generally indicated by reference numeral 100. The inside of the body 100 of the EPMA is maintained at a high vacuum of about $10^{-3}$ Pa by a vacuum pumping system (not shown). An electron gun 1 emitting an electron beam EB is incorporated in the body. The beam EB is sharply focused by an electron optical system 4 and made to hit a sample 2. The electron optical system 4 includes a condenser lens, an objective lens, and scan coils, and is controlled by a processor 12 via an electron optics control portion 9.

Characteristic X-rays 3 emanating from the sample 2 in response to the electron beam irradiation are spectrally resolved by an analyzing crystal 5 in a WDS (wavelength-dispersive X-ray spectrometer) 20 and detected by a detector 6. The WDS 20 includes the analyzing crystal 5, detector 6, and a WDS driver system 7. The WDS is controlled by the processor 12 via a WDS measurement control portion 8. Also, signals are accepted by the processor 12 via the WDS measurement control portion 8. Where plural WDS units are mounted, plural WDS (wavelength-dispersive X-ray spectrometer) units, each identical in structure with the WDS 20, are required.

The position (i.e., analysis point) of the electron beam EB on the sample 2 placed on a sample stage 10 can be moved in the X- and Y-directions (horizontal directions) and in the Z-direction (heightwise direction) by the processor 12 via a sample stage drive mechanism 11. Input devices 13 including a keyboard and a computer mouse and a display device (such as a liquid crystal monitor) 14 are connected with the processor 12.

Actual instrumentation includes many other components, such as a secondary electron detector, a backscattered electron detector, a power supply, a digital-to-analog converter, and an analog-to-digital converter, but they are not directly associated with the understanding of the present invention and so they are neither shown nor described.

The concept of the present invention is next described by referring to FIG. 1. In explaining the present invention, in a case where an X-ray spectrum is displayed as counts collected per given count time of to at each spectral position, the given count time of to is referred to as the reference count time. The square root of an arbitrary parameter X is denoted by Sqrt'X'.

In A of FIG. 1, it is assumed that X-ray counts not including any statistical fluctuations and collected for the time of to at some spectral position or the average counts obtained by repeating a measurement infinitely are N counts. Variation accompanying the X-ray N counts is indicated by a standard deviation of Eo, which is referred to as a statistically fluctuating component. Then, we have $$Eo=Sqrt'N'.$$

If one wants to reduce the variation below a certain magnitude Er (tolerable error for display) at any spectral position of the measured X-ray spectrum, the variation must be less than the variation of the magnitude of Er even at the spectral position indicated by N counts.

Accordingly, where Eo>Er, the time for which X-rays are counted is increased from to to tm as shown at C in FIG. 1. The total count is increased to Nm counts. If the total count is increased to Nm, the variation (standard deviation) Em also increases but the X-ray counts Nd actually used for spectral representation are normalized to counts collected for the time of to as indicated by B in FIG. 1. Consequently, the variation Ed of the displayed X-ray counts is also normalized and reduced.

That is, X-rays are counted while varying the count time according to the X-ray intensity at each spectral position such that the variation (tolerable error for display) Er of the displayed X-ray intensities is set equal to or less than a given value irrespective of the X-ray counts of the displayed X-ray spectrum. The obtained counts are converted into counts per given count time and used for analysis. The principle of the present invention has been described so far.

Measurement of an X-ray spectrum and method of display which make the variation of the displayed values of the X-ray intensities of the X-ray spectrum less than the tolerable error Er for display are next described in further detail.

The value of the tolerable error Er for display is determined prior to measurement of a waveform according to the accuracy of the waveform to be acquired. X-rays are counted for the count time of tm matched to the count rate I(cps) of the X-ray intensity at each spectral position. Thus, counts Nm (=I*tm) are obtained (see C of FIG. 1). The X-ray intensity Nd used when an X-ray spectral waveform is displayed is obtained by converting it into counts collected in the reference count time of to (see B of FIG. 1). At this time, variation due to statistical fluctuation of Nd is set equal to the tolerable error Er for display (see Eq. (5) below). That is, X-rays are counted only for the count time of tm in which the statistical fluctuation Sqrt(Nm) of the counts Nm multiplied by a factor of to/tm becomes equal to Er. Counts Nm collected for the time tm are obtained. The converted intensity Nd is found using Eq. (4) below and displayed.

$$Nd=Nm\times(to/tm) \quad (4)$$

Where the time tm is shorter than or equal to the time of to, the counting operation is terminated when the time of to elapses. Counts collected for the time of to are directly used as counts at the spectral position and displayed. In this case, the variation due to statistical fluctuations is less than the tolerable error Er for display.

Because the variation of Nd due to statistical fluctuations is set equal to the tolerable error Er for display, the error Er is given by $$(Sqrt(I\times tm))\times(to/tm)=Er \quad (5)$$

Accordingly, the count time of tm at the spectral position where the count rate of X-ray intensities is I(cps) is given by $$tm=I\times(to/Er)^2 \quad (6)$$

The count rate I(cps) of each X-ray intensity is found, using Eq. (7) below, from counts N collected for the reference count time of to.

$$I=N/to \quad (7)$$

The time of tm can be calculated, using Eq. (6).

Where the time of tm is shorter than or equal to the time of to, the counting operation is terminated when the time of to elapses. The obtained counts are directly displayed as counts at the spectral position. Where the time of tm is longer than the time of to, the counting operation is continued after the termination of the time of to until the count time reaches tm. The counts Nm collected for the time of tm are converted into counts Nd collected for the reference count time of to and displayed as counts at the spectral position.

With respect to the X-ray spectral waveform displayed by the method described above, the count time per point gives the counts collected for the time of to. The statistically fluctuating component (variation) of the X-ray intensity is equal to or less than the tolerable error Er for display at any spectral position.

Figure 3:
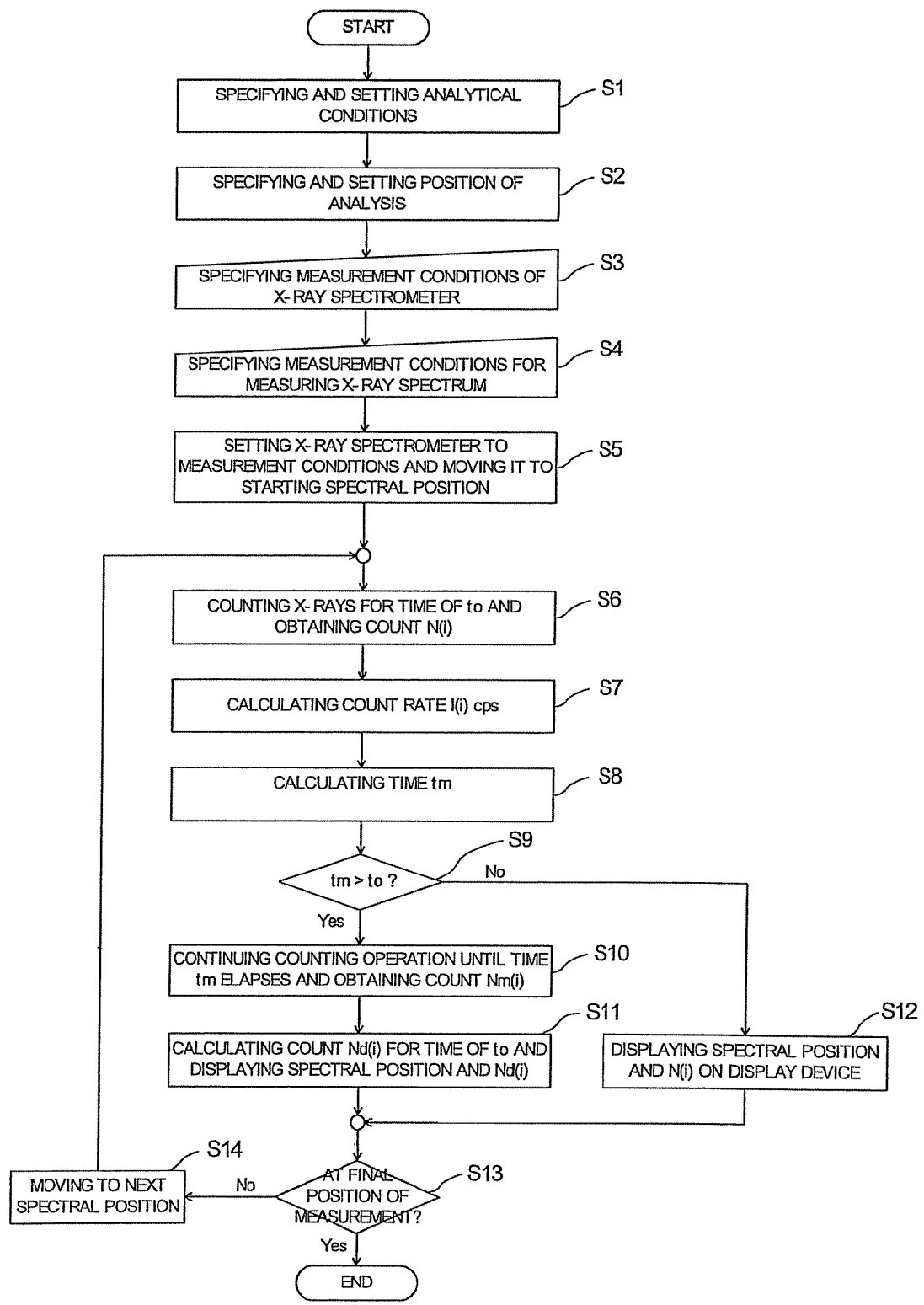
FIG. 3 is a flowchart illustrating an example of a sequence of procedures for embodying the present invention.
Figure 4:
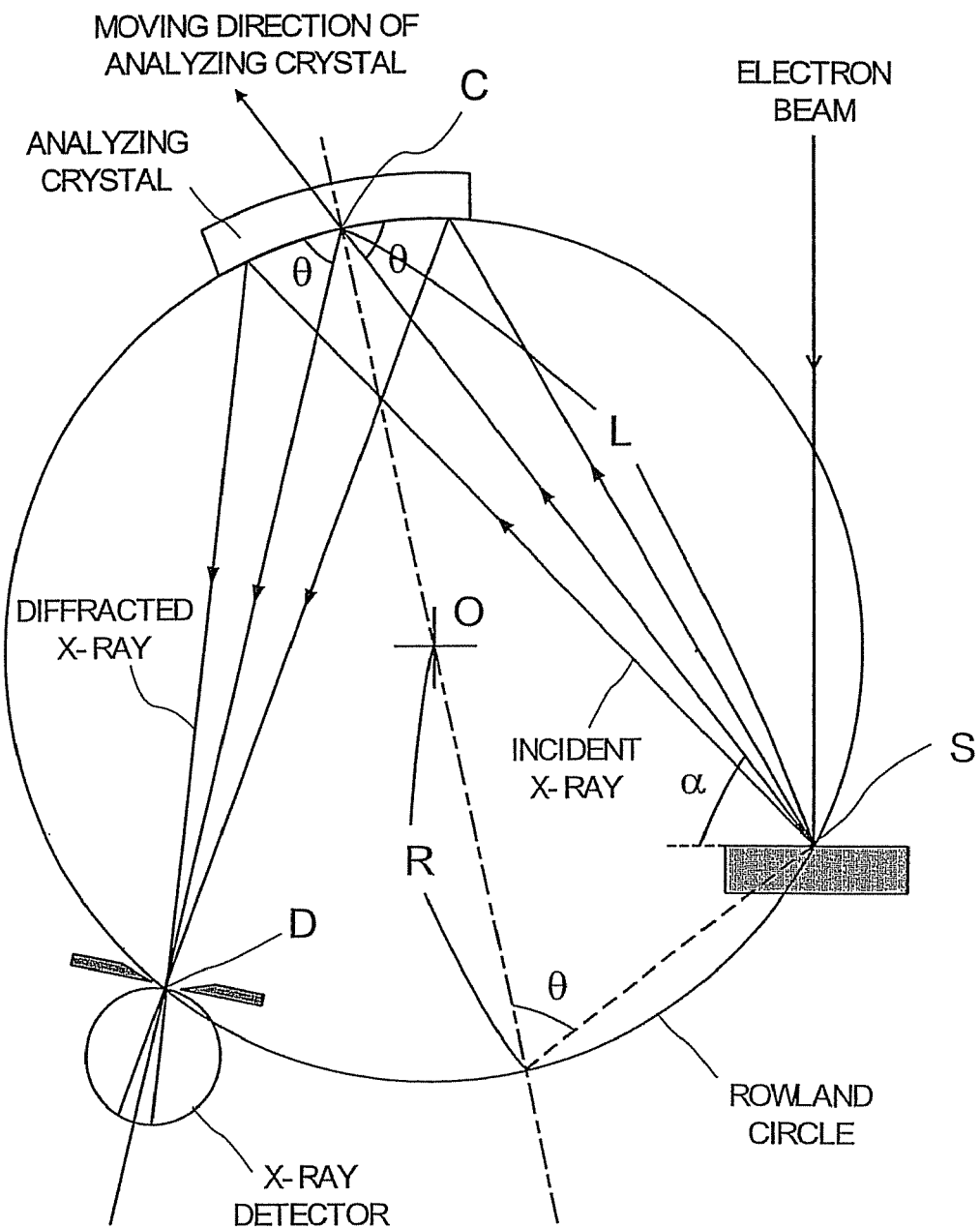
FIG. 4 is a diagram illustrating the principle of WDS equipped to EMPA.
Figure 6:
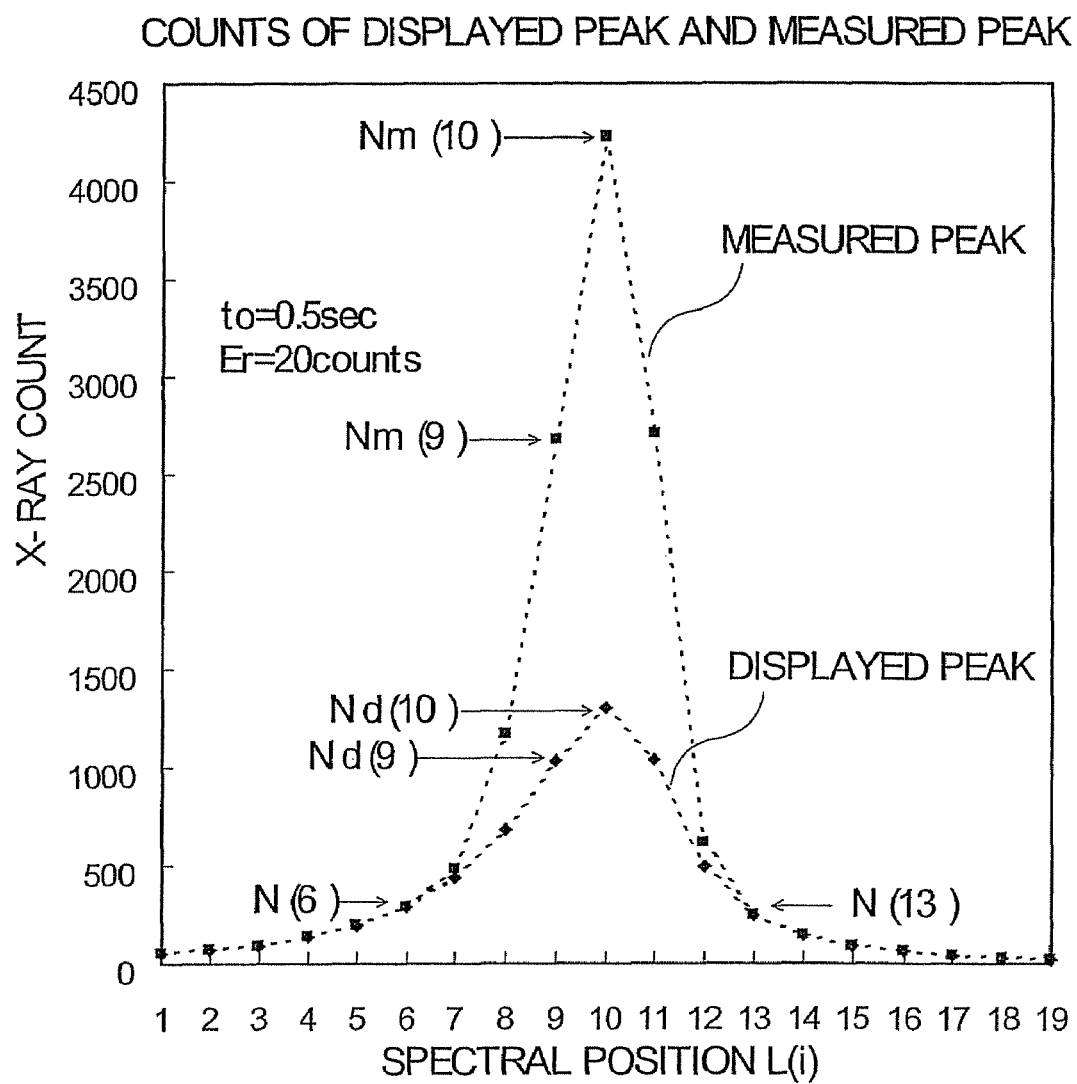
FIG. 6 is a graph illustrating the relationship between displayed peak intensity and measured peak intensity.

An example of a sequence of procedures for implementing the present invention is described by referring to the flowchart of FIG. 3 and also to FIGS. 2 and 6. The flowchart of FIG. 3 illustrates an example of a sequence of procedures performed in acquiring an X-ray spectrum using WDS equipped to EPMA. FIG. 6 is a schematic diagram illustrating the relationship between displayed counts collected from peaks and actually measured counts collected from peaks under the conditions where the reference count time to is 0.5 second and the tolerable error Er for display is 20 counts. The horizontal axis indicates spectral positions L(i), where i=1 to 19. The vertical axis indicates X-ray counts collected from peaks measured or displayed.

In step S1 of FIG. 3, the operator specifies analytical conditions (such as accelerating voltage, probe current value, and electron beam diameter) under which an X-ray spectrum is measured. The electron optical system 4 is set to conditions specified by the processor 12. In step S2, the operator specifies a position of analysis on the sample at which the X-ray spectrum is measured. The specimen stage driver mechanism 11 is driven under control of the processor 12 such that the position of analysis is brought into the beam position on the sample.

In step S3, the operator specifies measurement conditions of devices, such as the spectrometer and analyzing crystal used for measurement of the X-ray spectrum. In step S4, the operator specifies conditions under which the X-ray spectrum is measured, such as reference count time to, tolerable error Er for display, and spectral positions at the start and end of the measurement. In step S5, the processor 12 sets the X-ray spectrometer to the measurement conditions specified in steps S3 and S4 and brings the spectrometer into the spectral position where the measurement is started.

In step S6, X-rays are first counted for the time of to at the first spectral position L(1). As a result, counts N(1) at the spectral position L(1) are obtained. Operations in step S6 and subsequent steps are all automatically controlled by the processor 12. In step S7, the count rate I(1) is found from both to and N(1), using Eq. (7). In step S8, the time tm(1) is found from to, Er, and I(1), using Eq. (6).

In step S9, the lengths of the times to and tm(1) are compared. If tm(1)>to, the counting operation is continued until the time tm(1) elapses in step S10. As a result, Nm(1) is obtained. Subsequently, in step S11, the displayed counts Nd(1) are found from to, tm(1), and Nm(1), using Eq. (4). The counts Nd(1) are displayed as counts at the spectral position L(1). Then, control proceeds to step S13.

In step S9, if tm(1)≦to, the counting operation is terminated when the time of to has elapsed. N(1) collected for the time of to are directly displayed as counts at the spectral position L(1) in step 12. Then, control goes to step S13.

In step S13, a decision is made as to whether the spectral position is at the final position of measurement. If the spectral position is not yet at the final position, control goes to step S14. In step S14, the spectrometer moves to the next spectral position L(2), and the procedures of step S6 and subsequent steps are repeated. If the decision at step S13 is that the spectral position is at the final position of measurement, the measurement and display of the X-ray spectrum are ended.

Table 1 shows examples of parameters found by measurements performed under the conditions where the spectral position L(i) of FIG. 6 is given by i=6, 9, 10, and 13, as well as parameters found by calculations.

TABLE 1

| spectral position L(i) | counts N(i), in counts | count rate I(i), in counts | calculated time, tm(i), in sec | actual count time, to or tm(i), in sec | actual counts, N(i) or Nm(i), in counts | actual statistical fluctuation, Eo(i) or Em(i), in counts | displayed counts, N(i) or Nd(i), in counts | display error, Eo(i) or Ed(i), in counts |
|---|---|---|---|---|---|---|---|---|
| L(6) | 290 | 580.0 | 0.36 | 0.5 | 290 | 17.0 | 29.0 | 17.0 |
| L(9) | 1034 | 2068.0 | 1.29 | 1.29 | 2673 | 51.7 | 1034 | 20.0 |
| L(10) | 1300 | 2600.0 | 1.63 | 1.63 | 4225 | 65.0 | 1300 | 20.0 |
| L(13) | 244 | 488.0 | 0.31 | 0.5 | 244 | 15.6 | 244 | 15.6 | reference count time to = 0.5 s
display tolerable error Er = 20 counts

Note that the actual count time, actual counts, actual statistical fluctuation, displayed counts, and display error are different according to whether the time tm(i) is longer or shorter than the time of to as shown in FIG. 2.

TABLE 2

| | tm(i) ≦ to | tm(i) > to |
|---|---|---|
| actual count time | to | tm(i) |
| actual counts | N(i) | Nm(i) |
| actual statistical fluctuation | Eo(i) = Sqrt(N(i)) | Em(i) = Sqrt(Nm(i)) |
| displayed counts | N(i) | Nd(i) = Nm(i)*to/tm(i) |
| display error | Eo(i) = Sqrt(N(i)) | Ed(i) = Sqrt(Nm(i))*to/tm(i) |

Where the count rates Ip(cps) of peaks of the measured X-ray spectrum can be roughly estimated in advance, the display tolerable error Er can be determined as follows. That is, let Np be the counts collected for the reference count time of to at a spectral position near a peak. The tolerable value Kp of relative error of the displayed counts near the peak is determined. At this time, the tolerable error Er for display is given by $$Er = Np \times Kp \qquad (8)$$

If the error Er is determined in this way, the time tm can be found using Eq. (6). Consequently, in the same way as the procedures described previously, an X-ray spectral waveform in which the statistically fluctuating component of X-ray intensity is equal to or less than the display tolerable error Er at any spectral position can be obtained in one measurement and in bare minimum time.

In FIG. 6, if the vertical axis (X-ray counts) is displayed as a linear scale, the X-ray spectral waveform can be understood with greater ease. Furthermore, the advantages of the invention become more conspicuous.

The time tm calculated using Eq. (6) may be used up to an appropriate place of digit (such as to the order of 0.01 second).

In the above description, the count rate I(i) at each spectral position L(i) used for calculation of the time tm using Eq. (6) is found from the counts N(i) collected for the reference count time of to using Eq. (7). It is not always required that the count rates be found from the counts N(i) collected for the reference count time of to. Instead, the count rate may be found from counts collected for an appropriate time shorter than the time of to.

The vertical axis (X-ray intensity axis) used in displaying a final X-ray spectrum indicates counts N(i) (in the case where the time tm is shorter than or equal to the time of to) collected for the reference count time of to or converted counts Nd(i) (in the case where the time tm is longer than the time of to) that would have been collected for the time of to. Instead of these counts, their count rates may also be displayed on the assumption that I(i)=N(i)/to (in the case where tm≦to) or Id(i)=Nd(i)/to (in the case where tm>to) and converting the counts into count rates I(i) or Id(i).

In FIG. 6, the horizontal axis (spectral position) may be wavelength λ, energy, spectral position L, the value of 2θ, the value of θ, or the value of sin θ, where θ is the scattering angle, in the same way as the horizontal axis used where an X-ray spectrum is displayed by the prior art.

In the above embodiment of the present invention, the variation occurring when a measured X-ray spectrum is displayed is less than a given value. The present invention is not limited to this. For example, as already described in connection with the prior art, the present invention can also be used in a case where a simple quantitative analysis is performed, using main peaks arising from a chemical element identified from an X-ray spectrum collected by WDS. In this case, highest counts collected from characteristic X-ray peaks (in practice, a background value is subtracted from the counts) is divided by the previously found X-ray intensity of a standard sample, and the quotient is used as a relative intensity. A corrective calculation is performed on the relative intensity to find a weight concentration. That is, statistical fluctuations of the highest counts collected from characteristic X-ray peaks directly affect the accuracy of the simple quantitative value of an element contained at a relatively high concentration.

Figure 5:
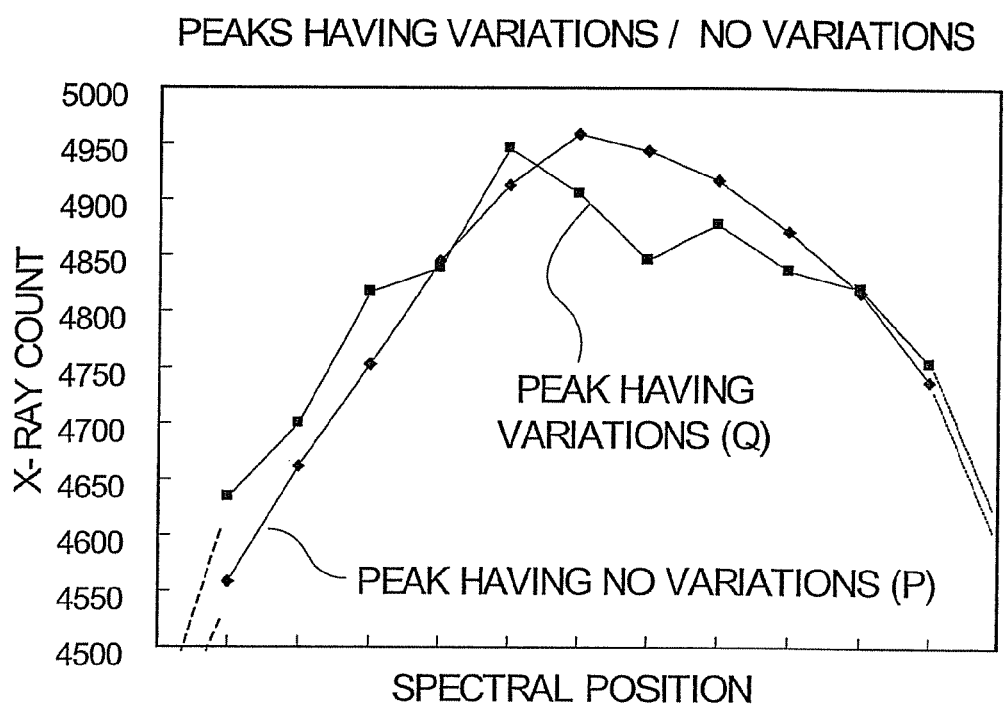
FIG. 5 is a graph illustrating differences in peak shape due to whether or not there is variation.

If the count time at each spectral position is prolonged in order to reduce variations in counts near peaks for obtaining peaks approximating nonfluctuating peaks (P) shown in FIG. 5, the total time taken to collect the X-ray spectrum will be exorbitantly long. On the other hand, where the present invention is used, simple quantitative values having less fluctuations can be obtained simply by increasing the count times near peaks producing especially high counts. Hence, the present invention can greatly contribute to improvement of the accuracy of analysis, in addition to improvement of display of a spectrum.

Having thus described my invention with the detail and particularity required by the Patent Laws, what is desired protected by Letters Patent is set forth in the following claims.

The invention claimed is:

1. A method of X-ray analysis using an X-ray spectrum obtained by a wavelength-dispersive X-ray spectrometer that detects and spectrally disperses X-rays produced from a sample irradiated with a beam of charged particles or X-rays, said method comprising the steps of:
making variable a time for which X-rays are counted at each spectral position;
converting obtained X-ray counts into X-ray counts to be collected per given count time in such a way that the magnitude of variation caused by statistical fluctuations of the X-ray counts to be collected per given count time is made equal to or less than a previously specified tolerance value at any spectral position; and
obtaining the X-ray spectrum using the X-ray counts obtained by the conversion.

2. A method of X-ray analysis as set forth in claim 1, wherein said X-ray spectrum is displayed based on the counts per given count time obtained by the conversion.

3. A method of X-ray analysis as set forth in claim 1, wherein said sample is analyzed quantitatively by using the counts per given count time obtained by the conversion as counts collected from characteristic X-ray peaks arising from elements contained in the sample.

4. A method of X-ray analysis as set forth in claim 1 or 2, wherein a reference count time for which X-rays are counted at the spectral positions is previously set, and wherein the count rates at the spectral positions are found from counts collected for the reference count time and from the reference count time.

5. A method of X-ray analysis as set forth in claim 4, wherein a time for which counting is continued at the spectral positions after passage of said reference count time is determined based on (i) said count rates at the spectral positions, (ii) said reference count time, and (iii) said tolerance value.

6. A method of X-ray analysis as set forth in claim 4, wherein said reference count time is used as said given count time.

7. A method of X-ray analysis as set forth in claim 1 or 2, wherein the X-ray wavelength axis of said X-ray spectrum or an axis corresponding to the X-ray wavelength axis indicates at least one of wavelength, energy, a spectral position indicative of the distance from a point at which X-rays are produced to the center of an analyzing crystal, the value of 2θ, the value of θ, and the value of sin θ, where θ is the scattering angle of the analyzing crystal.

8. An X-ray analysis apparatus using an X-ray spectrum obtained by a wavelength-dispersive X-ray spectrometer that detects and spectrally disperses X-rays produced from a sample irradiated with a beam of charged particles or X-rays,
wherein a time for which X-rays are counted at each spectral position is made variable,
wherein obtained X-ray counts are converted into X-ray counts to be collected per given count time in such a way that the magnitude of variation caused by statistical fluctuations of the X-ray counts to be collected per given count time is made equal to or less than a previously specified tolerance value at any spectral position, and
wherein the X-ray spectrum is obtained using the X-ray counts obtained by the conversion.

9. An X-ray analysis apparatus as set forth in claim 8, wherein said X-ray spectrum is displayed based on the counts per given count time obtained by the conversion.

10. An X-ray analysis apparatus as set forth in claim 8, wherein said sample is analyzed quantitatively by using the counts per given count time obtained by the conversion as counts collected from characteristic X-ray peaks arising from elements contained in the sample.

11. An X-ray analysis apparatus as set forth in claim 8 or 9, wherein a reference count time for which X-rays are counted at the spectral positions is previously set, and wherein the count rates at the spectral positions are found from counts collected for the reference count time and from the reference count time.

12. An X-ray analysis apparatus as set forth in claim 11, wherein a time for which counting is continued at the spectral positions after passage of said reference count time is determined based on (i) said count rates at the spectral positions, (ii) said reference count time, and (iii) said tolerance value.

13. An X-ray analysis apparatus as set forth in claim 11, wherein said reference count time is used as said given count time.

14. An X-ray analysis apparatus as set forth in claim 8 or 9, wherein the X-ray wavelength axis of the X-ray spectrum or an axis corresponding to the X-ray wavelength axis indicates at least one of wavelength, energy, a spectral position indicative of the distance from a point at which X-rays are produced to the center of an analyzing crystal, the value of $2\theta$, the value of $\theta$, and the value of $\sin \theta$, where $\theta$ is the scattering angle of the analyzing crystal.

* * * * *